(12) United States Patent
Harrah et al.

(10) Patent No.: US 12,256,914 B2
(45) Date of Patent: Mar. 25, 2025

(54) ACCESS DEVICE HAVING AN ANCHORING FEATURE AND METHODS OF USING THE SAME

(71) Applicant: Boston Scientific Limited, Hamilton (BM)

(72) Inventors: Timothy P. Harrah, Cambridge, MA (US); Christopher L. Oskin, Grafton, MA (US); Arpita Banerjee, Bangalore (IN); Abhijit Takale, Maharashtra (IN); Sandesh Gavade, Bangalore (IN); Pavan Misra, Bangalore (IN)

(73) Assignee: Boston Scientific Limited, Hamilton (BM)

( * ) Notice: Subject to any disclaimer, the term of this patent is extended or adjusted under 35 U.S.C. 154(b) by 615 days.

(21) Appl. No.: 17/301,832

(22) Filed: Apr. 15, 2021

(65) Prior Publication Data

US 2021/0228199 A1 Jul. 29, 2021

Related U.S. Application Data

(63) Continuation of application No. 15/412,864, filed on Jan. 23, 2017, now Pat. No. 11,006,941.
(Continued)

(51) Int. Cl.
*A61B 17/02* (2006.01)
*A61B 17/34* (2006.01)
*A61B 17/00* (2006.01)

(52) U.S. Cl.
CPC ...... *A61B 17/0218* (2013.01); *A61B 17/3421* (2013.01); *A61B 2017/00477* (2013.01);
(Continued)

(58) Field of Classification Search
CPC ............ A61B 17/0218; A61B 17/02; A61B 2017/0225; A61B 17/3421; A61B 17/3423
See application file for complete search history.

(56) References Cited

U.S. PATENT DOCUMENTS

| 4,043,346 A | 8/1977 | Mobley et al. |
| 4,924,851 A | 5/1990 | Ognier et al. |

(Continued)

FOREIGN PATENT DOCUMENTS

| CN | 103393449 A | 11/2013 |
| CN | 103917179 A | 7/2014 |

(Continued)

OTHER PUBLICATIONS

Communication pursuant to Article 94(3) EPC for European Application No. 17704132.4, mailed Mar. 4, 2020, 4 pages.
(Continued)

*Primary Examiner* — Amy R Sipp
(74) *Attorney, Agent, or Firm* — Brake Hughes Bellermann LLP

(57) ABSTRACT

According to an aspect, a medical device includes an elongate member and a sleeve. The elongate member defines a lumen and has a first end portion and a second end portion. The second end portion has a first configuration and a second configuration. The second end portion has a first size when the second end portion is in its first configuration and a second size when the second end portion is in its second configuration. The first size is smaller than the second size. The second end portion is biased to its second configuration. The sleeve defines a lumen extending from a first end portion of the sleeve to a second end portion of the sleeve.

16 Claims, 7 Drawing Sheets

Related U.S. Application Data

(60) Provisional application No. 62/288,925, filed on Jan. 29, 2016.

(52) U.S. Cl.
CPC ............ *A61B 2017/00858* (2013.01); *A61B 2017/00951* (2013.01); *A61B 2017/0225* (2013.01); *A61B 2017/347* (2013.01); *A61B 2017/3484* (2013.01); *A61B 2017/3488* (2013.01)

(56) References Cited

U.S. PATENT DOCUMENTS

| | | | |
|---|---|---|---|
| 5,707,359 A * | 1/1998 | Bufalini | A61B 17/3421 606/198 |
| 5,817,062 A | 10/1998 | Flom et al. | |
| 6,228,059 B1 | 5/2001 | Astarita | |
| 11,006,941 B2 * | 5/2021 | Harrah | A61B 17/3421 |
| 2004/0039400 A1 | 2/2004 | Schmieding et al. | |
| 2004/0225192 A1 | 11/2004 | Young et al. | |
| 2005/0004434 A1 | 1/2005 | Bob et al. | |
| 2005/0096507 A1 | 5/2005 | Prosek | |
| 2005/0192532 A1 | 9/2005 | Kucklick et al. | |
| 2007/0088275 A1 | 4/2007 | Stearns et al. | |
| 2007/0173754 A1 | 7/2007 | Kucklick et al. | |
| 2007/0213675 A1 * | 9/2007 | Albrecht | A61B 17/3421 604/264 |
| 2009/0105691 A1 | 4/2009 | Sung | |
| 2011/0144440 A1 | 6/2011 | Cropper et al. | |
| 2012/0095291 A1 | 4/2012 | Nakajima et al. | |
| 2013/0178709 A1 | 7/2013 | Suh et al. | |
| 2013/0197592 A1 * | 8/2013 | Mafi | A61B 17/3421 606/323 |
| 2014/0171873 A1 * | 6/2014 | Mark | A61B 17/3417 604/164.01 |
| 2014/0303669 A1 | 10/2014 | Richard | |
| 2014/0343366 A1 | 11/2014 | Coe et al. | |

FOREIGN PATENT DOCUMENTS

| | | |
|---|---|---|
| WO | 0062689 A1 | 10/2000 |
| WO | 2008030256 A1 | 3/2008 |

OTHER PUBLICATIONS

First Office Action for Chinese Application No. 201780008953.4 (with English Translation), mailed Sep. 16, 2020, 23 pages.
International Search Report and Written Opinion for PCT Application No. PCT/US2017/014700, mailed Mar. 28, 2017, 12 pages.

* cited by examiner

ACCESS DEVICE HAVING AN ANCHORING FEATURE AND METHODS OF USING THE SAME

CROSS-REFERENCE TO RELATED APPLICATIONS

This application is a continuation of, and claims priority to, U.S. patent application Ser. No. 15/412,864, filed on Jan. 23, 2017, entitled "ACCESS DEVICE HAVING AN ANCHORING FEATURE AND METHODS OF USING THE SAME", which claims priority to U.S. Patent Application No. 62/288,925, filed on Jan. 29, 2016, entitled "ACCESS DEVICE HAVING AN ANCHORING FEATURE AND METHODS OF USING THE SAME", the disclosures of which are incorporated by reference herein in their entirety.

TECHNICAL FIELD

This disclosure relates generally to medical devices and more particularly to medical devices such as access devices or sheaths that include anchoring features.

BACKGROUND

A variety of medical procedures are performed using an access device or an access sheath. For example, access devices or access sheaths may be used in procedures such as percutaneous nephrolithotomy procedures.

In some procedures that use access devices or access sheaths, it may be difficult for a physician or other medical practitioner to maintain the placement of the access device or the access sheath within the body of the patient during the entire procedure. In some cases, the access device or the access sheath may move within the body or be unintentionally dislodged from its desired position within the body of the patient.

Accordingly, it may be desirable to provide a device, such as an access device or access sheath that includes features or components that help facilitate the securement of the access device or access sheath within the body of the patient.

SUMMARY

According to an aspect, a medical device includes an elongate member and a sleeve, The elongate member defines a lumen and has a first end portion and a second end portion. The second end portion has a first configuration and a second configuration. The second end portion has a first size when the second end portion is in its first configuration and a second size when the second end portion is in its second configuration. The first size is smaller than the second size. The second end portion is biased to its second configuration. The sleeve defines a lumen extending from a first end portion of the sleeve to a second end portion of the sleeve. The lumen is configured to movably receive at least a portion of the elongate member. The sleeve is configured to engage the second end portion of the elongate member to help retain the second end portion of the elongate member in its first configuration.

In some embodiments, the lumen defined by the elongate member extends from the first end portion of the elongate member to the second end portion of the elongate member.

In some embodiments, the elongate member defines a longitudinal axis, the at least a portion of the elongate member being movably received by the sleeve such that the elongate member may move in a direction substantially parallel to the longitudinal axis of the elongate member.

In some embodiments the elongate member is configured to rotate with respect to the sleeve.

In some embodiments, the elongate member includes a hub member, the hub member defines an opening, the opening being in fluid communication with the lumen of the elongate member. In some embodiments, the elongate member includes a hub member, the hub member defines a funnel shaped opening, the funnel shaped opening being in fluid communication with the lumen of the elongate member.

In some embodiments, the elongate member having a longitudinal length, the sleeve having a longitudinal length, the longitudinal length of the elongate member being greater than the longitudinal length of the sleeve.

In some embodiments, the second end portion of the elongate member includes a plurality of support members.

In some embodiments, the elongate member is configured to be locked in position with respect to the sleeve. In some embodiments, the elongate member is configured to be locked in position with respect to the sleeve via a frictional coupling between a portion of the elongate member and a portion of the sleeve. In some embodiments, the elongate member includes a first locking feature, the sleeve includes a second locking feature, the first locking feature being configured to engage the second locking feature to lock the elongate member with respect to the sleeve.

In some embodiments, the lumen of the elongate member is configured to receive a secondary medical device.

In some embodiments, the sleeve includes an inner surface, at least a portion of the inner surface of the sleeve being configured to engage the second end portion of the elongate member to help retain the elongate member in its first configuration.

In some embodiments, the medical device is configured to be inserted into a body of a patient. In some embodiments, the medical device is configured to be inserted into a body of a patient and the lumen of the elongate member is configured to receive at least a portion of a secondary medical device.

In another aspect, a medical device includes an elongate member and a sleeve. The elongate member defines a lumen and has a first end portion and a second end portion. The second end portion has a first configuration and a second configuration. The second end portion has a first size when the second end portion is in its first configuration and a second size when the second end portion is in its second configuration. The first size being smaller than the second size. The second end portion is biased to its second configuration. The sleeve is movably coupled to the elongate member. The sleeve has a contact surface. The contact surface is configured to contact the second end portion of the elongate member to help retain the elongate member in its first configuration.

In some embodiments, the elongate member is configured to rotate with respect to the sleeve. In some embodiments, the elongate member includes a hub member, the hub member defines an opening, the opening being in fluid communication with the lumen of the elongate member. In some embodiments, the elongate member includes a hub member, the hub member defines a funnel shaped opening, the funnel shaped opening being in fluid communication with the lumen of the elongate member.

In some embodiments, the second end portion of the elongate member includes a plurality of support members.

In some embodiments, a method includes inserting a medical device into a body of a patient, the medical device including an elongate member and a sleeve; and moving the elongate member with respect to the sleeve such that an end portion of the elongate member moves away from an end portion of the sleeve and moves from a collapsed configuration to an expanded configuration. In some embodiments, the moving the elongate member with respect to the sleeve includes rotating the elongate member with respect to the sleeve.

DETAILED DESCRIPTION

Detailed embodiments are disclosed herein. However, it is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the invention.

The terms "a" or "an," as used herein, are defined as one or more than one. The term "another," as used herein, is defined as at least a second or more. The terms "including" and/or "having", as used herein, are defined as comprising (i.e., open transition).

The term patient may hereafter be used for a person who benefits from the medical device or the methods disclosed in the present application. For example, the patient can be a person whose body is operated through the medical device or the method disclosed by the present invention. For example, in some aspects, the patient may be a human female, a human male, or any other mammal.

The terms proximal and distal described in relation to various devices, apparatuses, and components as discussed in the subsequent text of the present application are referred with a point of reference. The point of reference, as used in this description, is a perspective of an operator. The operator may be a surgeon, a physician, a nurse, a doctor, a technician, and the like who may perform the procedure and operate the medical device as described in the present invention. The term proximal refers to an area or portion that is closer or closest to the operator during a surgical procedure. The term distal refers to an area or portion that is farther or farthest from the operator.

Figure 1:
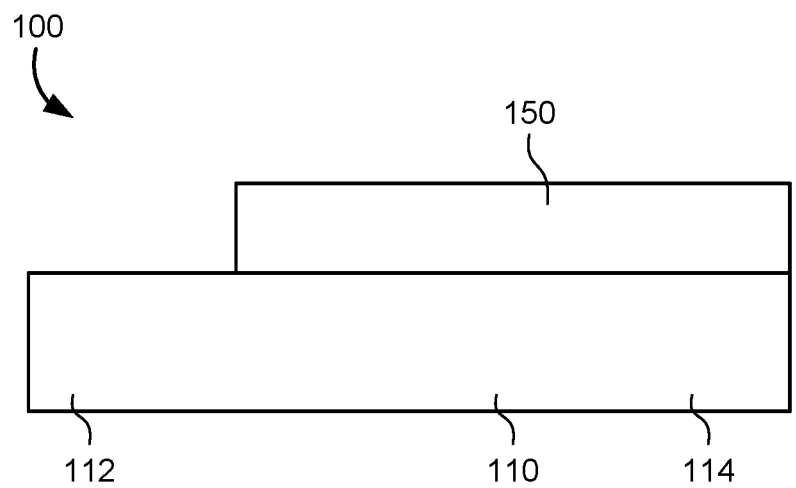
FIG. 1 is a schematic illustration of a medical device according to an embodiment.

FIG. 1 is a schematic illustration of a medical device 100 according to an embodiment of the invention. The medical device 100 may be used in surgical procedures. For example, in some embodiments the medical device 100 may be placed within a body of a patient to create an access or port for further medical procedures. More specifically, in some embodiments, the medical device 100 may be placed within the body of the patient such that a distal end portion of the medical device 100 is disposed within the body of the patient and a proximal end portion of the medical device 100 extends from the body of the patient. In some embodiments, an additional or secondary medical device may be inserted into the body of the patient via the medical device 100 to perform an additional medical procedure.

In the illustrated embodiment, the medical device 100 includes an elongate member 110 and a sleeve 150. The elongate member 110 has a first or proximal end portion 112 and a second or distal end portion 114. In some embodiments, the elongate member 110 defines a lumen that extends from the first or proximal end portion 112 to the second or distal end portion 114.

In some embodiments, the elongate member 110 is linear or substantially straight or linear. In other embodiments, the elongate member 110 is curved or is flexible and may form a curve or have a curved portion. In some embodiments, the elongate member 110 may be tubular or have a round or circular cross-sectional shape. In other embodiments, the elongate member 110 has a different cross-sectional shape, such as square, rectangular, triangular, or any other shape.

In some embodiments, second or distal end portion 114 of the elongate member 110 may be placed in a first configuration (or collapsed configuration) or a second configuration (or expanded configuration). The second end portion 114 of the elongate member 110 has a first size when the second end portion 114 is in its first configuration. The second end portion 114 has a second size when the second end portion 114 is in its second configuration. The first size is smaller than the second size. In some embodiments, the second end portion 114 is biased to its second or expanded configuration.

The sleeve 150 is movably coupled to the elongate member 110. In some embodiments, the sleeve 150 defines a lumen. In such embodiments, the lumen may receive at least a portion of the elongate member 110 such that the elongate member 110 may move with respect to the sleeve 150.

The sleeve 150 is configured to retain the second end portion 114 of the elongate member in its first or collapsed configuration. In some embodiments, the sleeve 150 includes a contact portion or a contact surface. The contact portion or the contact surface is configured to contact the second end portion 114 of the elongate member 110 to help retain or force the second end portion 114 of the elongate member 110 in its first or collapsed configuration.

In use, the medical device 100 may be inserted into a body of a patient. In some embodiments, the medical device 100 may be inserted into the body of the patient while the second end portion 114 of the elongate member 110 is in its first or collapsed configuration. For example, in some embodiments, the medical device 100 may be inserted into the body of the patient while the contact portion or contact surface of the sleeve 150 is in contact with the second end portion 114 of the elongate member 110 to retain the second end portion 114 of the elongate member 110 in its first or collapsed configuration.

In some embodiments, the medical device 100 may be inserted into the body of the patient such that the second or distal end portion 114 of the elongate member 110 is disposed within the body of the patient and the first or proximal end portion 112 of the elongate member 110 is disposed outside of the body of the patient (or extends from the body of the patient).

The second end portion 114 may then be moved from its first or collapsed configuration to its second or expanded configuration. For example, in some embodiments, the elongate member 110 is moved with respect to the sleeve 150 such that the contact portion or contact surface of the sleeve disengages or is removed from the second end portion 114 of the elongate member 110. The second end portion 114 of the elongate member 110 may then move to its second or expanded configuration. In some embodiments, the second end portion 114 of the elongate member 110 is biased to its second or expanded configuration and will move to such configuration in the absences of an external or retaining force.

In some embodiments, the second end portion 114 of the elongate member 110 is configured to retain or help retain the medical device 100 in place within the body of the patient. Specifically, in some embodiments, the second end portion 114 in its second or expanded configuration is configured to contact bodily tissue of the patient to retain or help retain the medical device 100 in place within the body of the patient.

In some embodiments, the elongate member 110 defines a lumen. Once the medical device 100 is disposed within the body of the patient, other medical devices may be inserted into the body of the patient though the lumen defined by the elongate member 110. Accordingly, such other or secondary medical devices may be used to perform additional medical procedures once such device is disposed within the body of the patient.

Figure 2:
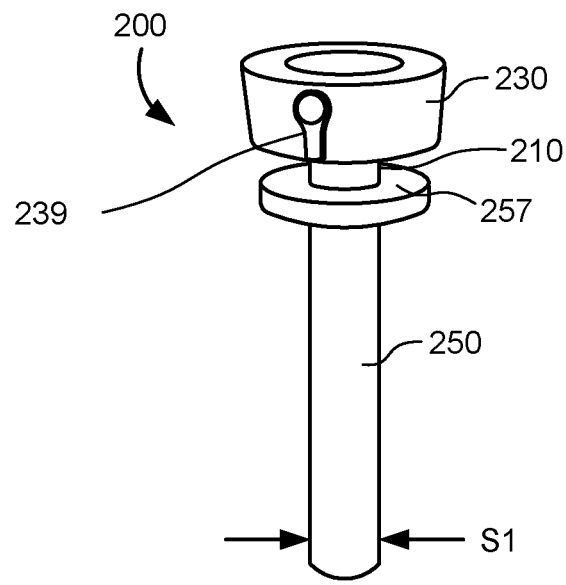
FIGS. 2 and 3A are side views of a medical device according to an embodiment.
Figure 3A:
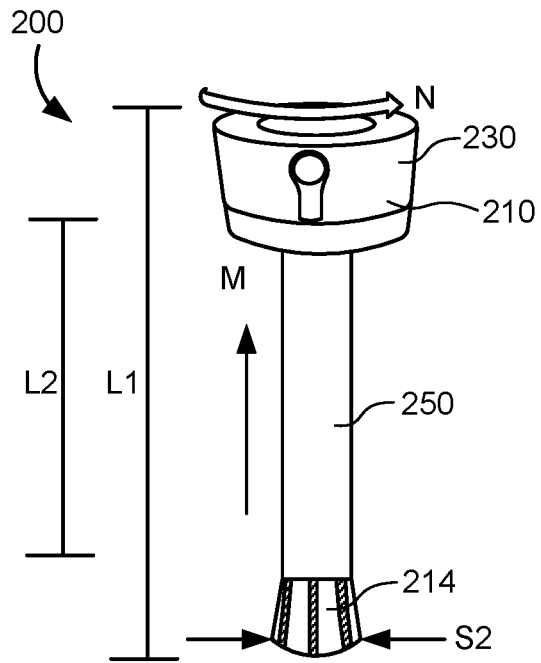
Figure 3B:
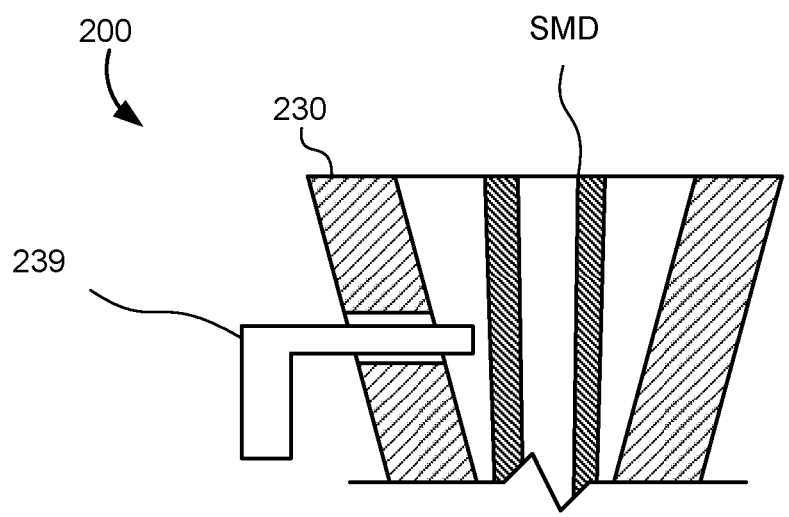
FIG. 3B is a cross-sectional view of a portion of the medical device of FIGS. 2 and 3A.
Figure 11:
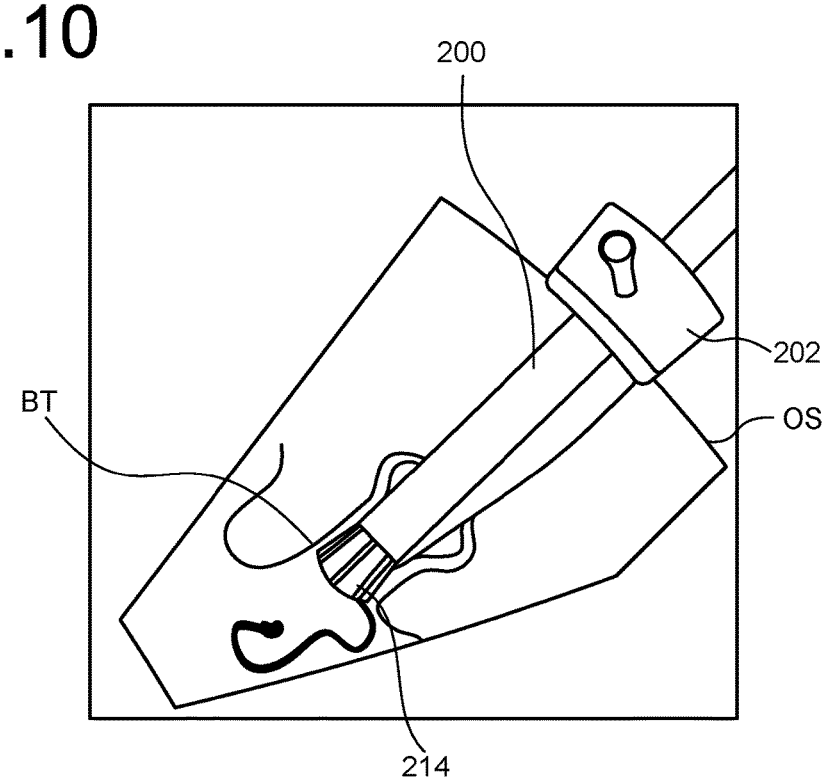
FIG. 11 is a schematic view of the medical device of FIGS. 2 and 3A disposed within a body of a patient.

FIGS. 2 and 3A are side views of a medical device 200 according to an embodiment of the invention. FIG. 3B is a cross-sectional view of a portion of the medical device 200. The medical device 200 may be used in surgical procedures. For example, in some embodiments the medical device 200 may be placed within a body of a patient to create an access or port for further medical procedures. For example, in some embodiments, the medical device 200 may be placed within a body of a patient and used in a percutaneous nephrolithotomy procedure. In some embodiments, as best illustrated in FIG. 11, the medical device 200 may be placed within the body of the patient such that a distal end portion of the medical device 200 is disposed within the body of the patient and a proximal end portion of the medical device 200 extends from the body of the patient. In some embodiments, an additional or secondary medical device may be inserted into the body of the patient via the medical device 200 to perform an additional medical procedure.

In the illustrated embodiment, the medical device 200 includes an elongate member 210 and a sleeve 250. As will be described in more detail below, FIG. 2 illustrates the elongate member 210 with its distal end portion 214 in a first or collapsed configuration and FIG. 3A illustrates the elongate member 210 with its distal end portion 214 in a second or expanded configuration.

Figure 4:
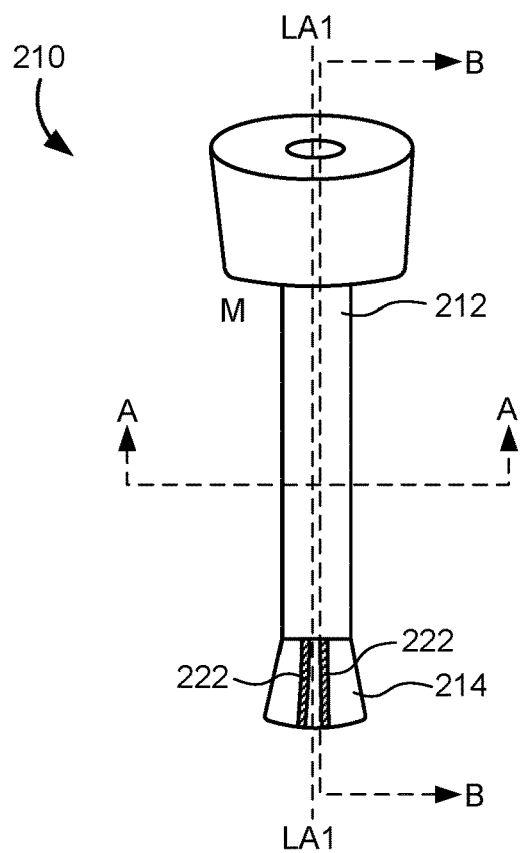
FIG. 4 is a side view of an elongate member of the medical device of FIGS. 2 and 3A.
Figure 5:
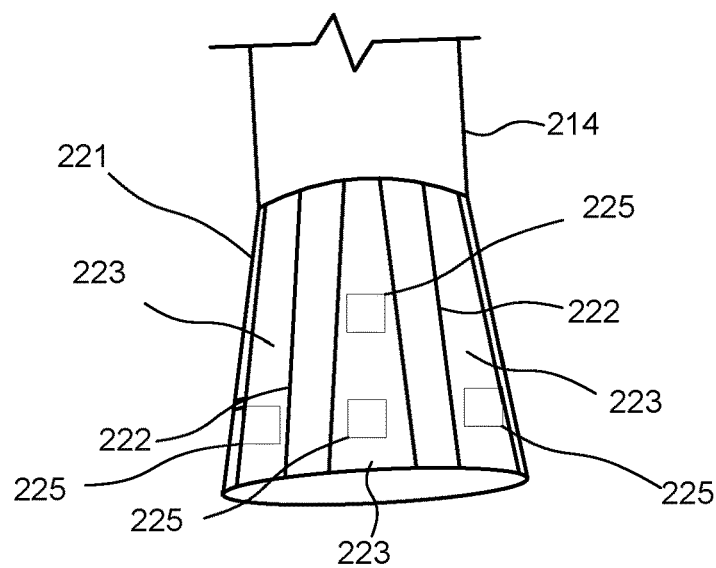
FIG. 5 is a side view of a distal end portion of the elongate member of FIG. 4.
Figure 6:
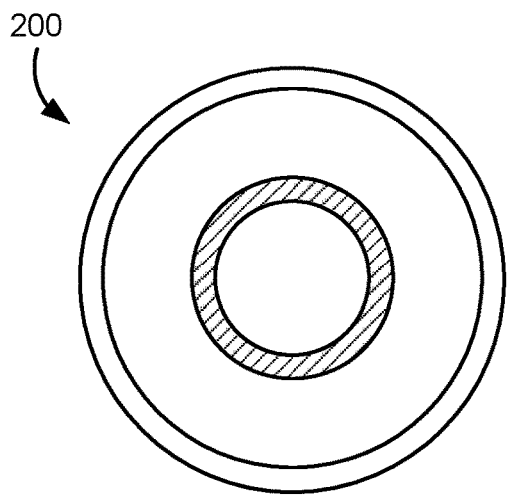
FIG. 6 is a cross-sectional view of the elongate member of FIG. 4 taken along line A-A of FIG. 4.
Figure 7:
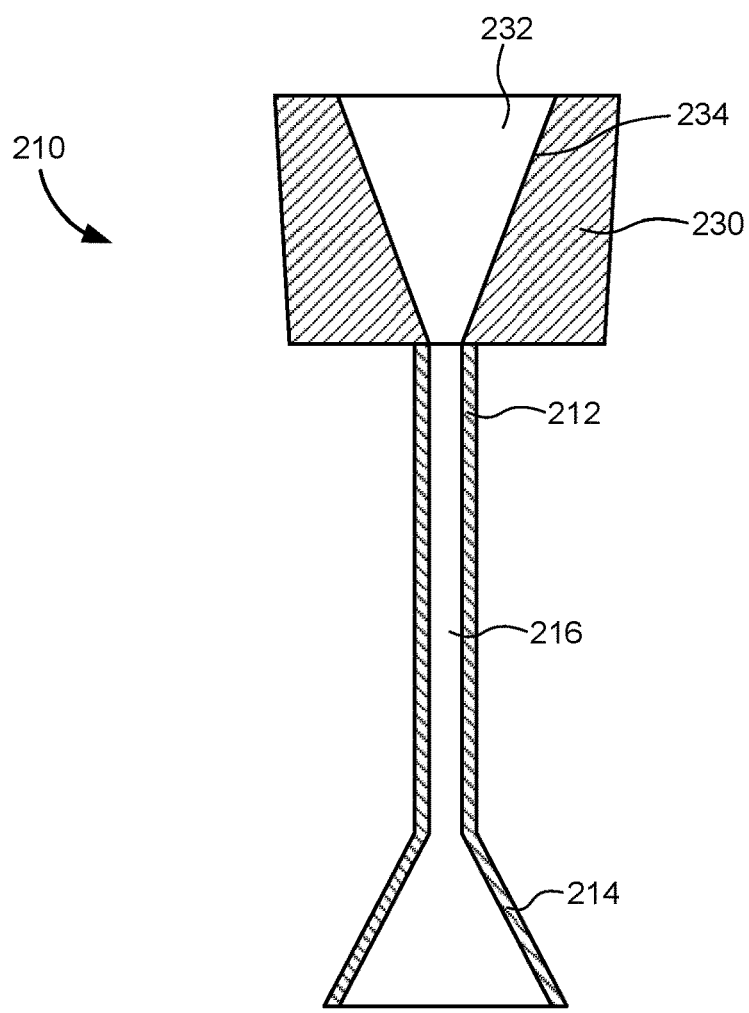
FIG. 7 is a cross-sectional view of the elongate member of FIG. 4 taken along line B-B of FIG. 4.

FIG. 4 is a side view of the elongate member 210. FIG. 5 is a side view of the distal end portion 214 of the elongate member 210. FIG. 6 is a cross-sectional view of the elongate member 210 taken along line A-A of FIG. 4. FIG. 7 is a cross-sectional view of the elongate member 210 taken along line B-B of FIG. 4.

The elongate member 210 has a first or proximal end portion 212 and a second or distal end portion 214. The elongate member 210 defines a lumen 216 that extends from the first or proximal end portion 212 to the second or distal end portion 214.

In the illustrated embodiment, the elongate member 210 is linear or substantially linear. Specifically, the elongate member 210 extends along a longitudinal axis LA1. In other embodiments, the elongate member 210 is curved or is flexible and may form a curve or have a curved portion.

As best illustrated in FIG. 6, the elongate member 210 may be tubular or have a round or circular cross-sectional shape (the cross-section that is disposed orthogonal or substantially orthogonal to the longitudinal axis LA1 of the elongate member 210). In other embodiments, the elongate member 210 has a different cross-sectional shape, such as square, rectangular, triangular, or any other shape.

The second or distal end portion 214 of the elongate member 210 may be placed in a first configuration (or collapsed configuration) or a second configuration (or expanded configuration). The second end portion 214 of the elongate member 210 has a first size S1 when the second end portion 214 is in its first configuration. For example, as will be described in detail below and as illustrated in FIG. 2, the second end portion 214 is in its first configuration and has a size or width S1 when the second end portion 214 is disposed within the sleeve 250. The second end portion 214 has a second size or width S2 when the second end portion 214 is in its second configuration. As best illustrated in FIG. 3A, the second end portion 214 is in its second configuration and has the second size S2 when the second end portion 214 is disposed outside of the sleeve 250. The first size S1 is smaller than the second size S2.

In the illustrated embodiment, the second end portion 214 is biased to its second or expanded configuration. In some embodiments, the second end portion is biased to a flared configuration or shape. As best illustrated in FIG. 5, the second end portion 214 includes support members 222 that extend longitudinally or substantially longitudinally. The support members 222 are configured to expand or separate when the second end portion 214 is disposed outside of the sleeve 250. In some embodiments, the support members 222 are formed of a biocompatible material. In some embodiments, the support members 222 are formed of the same material that is used to form the sleeve 250. In some embodiments, the support members 222 have a thickness that is larger than the thickness of the sleeve 250. Extension portions 223 extend between the support members 222. In some embodiments, the extension portions 223 are more flexible than the support members 222. In some embodiments, the flexibility of the extension portions 223 facilitates the expansion of the second end portion 214 to its larger or flared configuration. In some embodiments, the extension portions 223 are formed of a material that is more flexible than the material that is used to form the support members 222. In some embodiments, the second end portion 214 can be formed of a molded thermoplastic or a shaped metal material or a metal support on a polymeric member. In some embodiments, the support members 222 may be formed of acetal or polyetherimide. In other embodiments, the support members 222 are formed of polyethylene, polypropylene, polyvinyl chloride, nitinol or stainless steel.

In some embodiments, an outer surface 221 of the second end portion 214 is configured to grip or adhere to bodily tissue of the patient to help retain the device 200 in place within the body of the patient. In some embodiments, the outer surface 221 includes an material or a coating that has a relatively high coefficient of friction to help grip or adhere to the bodily tissue or anatomy of the patient. In some embodiments, the second end portion 214 includes anchoring members or points 225. The anchoring members or points 225 may be raised or protruding portions that help the second end portion 214 grip or adhere to the bodily tissue or anatomy of the patient when the device is in its expanded configuration. The anchoring members or points 225 may be of any shape or size. In some embodiments, the anchoring members or points 225 are rectangular in shape. In other embodiments, the anchoring members or points 225 are circular in shape. In some embodiments, the anchoring members or points 225 may be circumferentially distributed or arraigned in a row or a plurality of rows.

In some embodiments, a gel may coat or cover a portion of the anchoring members 225. The gel may be a biodegradable or medical gel and may have a relatively high coefficient of friction. Thus, in some embodiments, the gel may help the second end portion 214 grip or adhere to the bodily tissue or anatomy of the patient when the device is in its expanded configuration. In some embodiments, the gel may be gel pads. In some embodiments, the gel may be or include a silicone gel.

Figure 8:
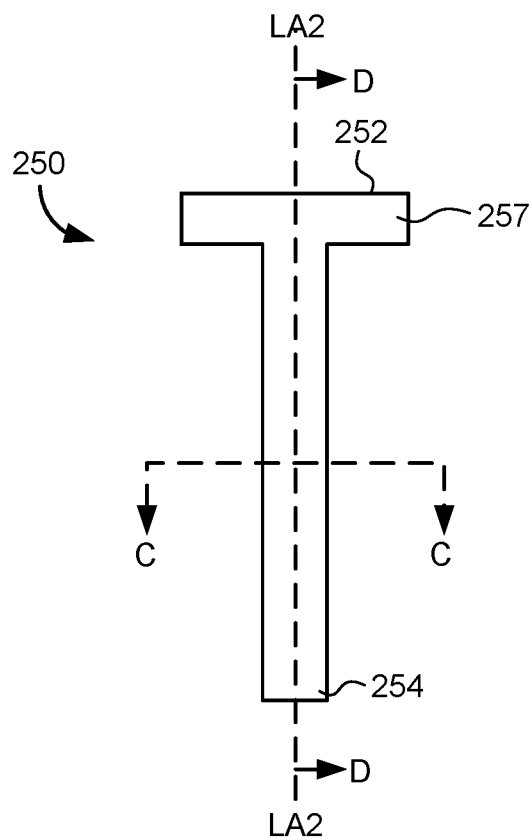
FIG. 8 is a side view of a sleeve of the medical device of FIGS. 2 and 3A.
Figure 9:
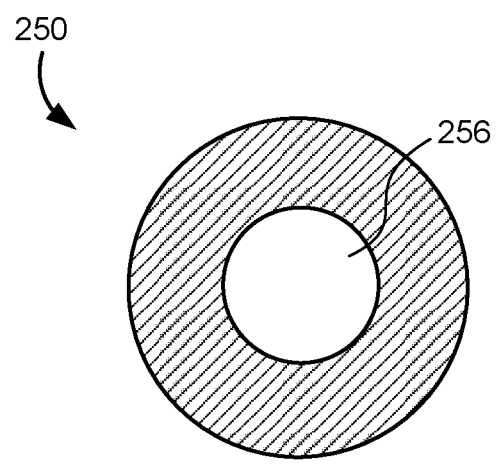
FIG. 9 is a cross-sectional view of the sleeve of FIG. 8 taken along line C-C of FIG. 8.
Figure 10:
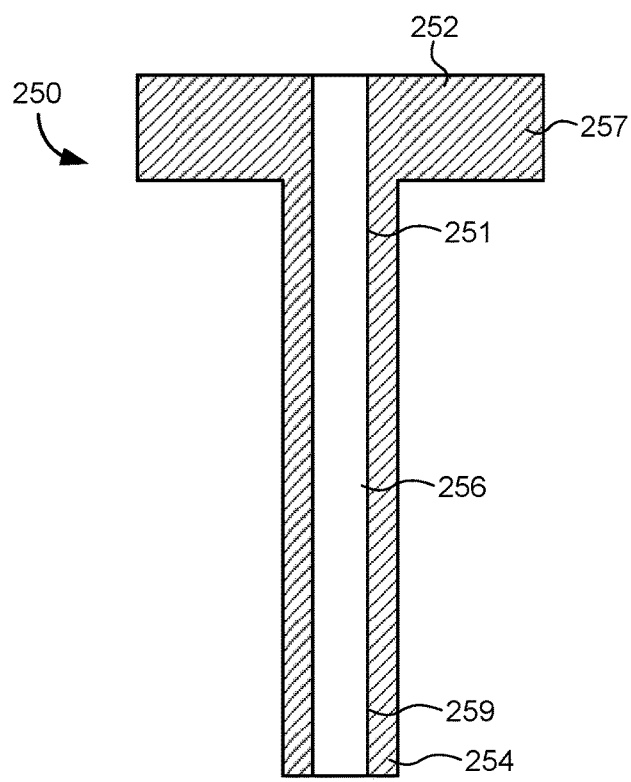
FIG. 10 is a cross-sectional view of the sleeve of FIG. 8 taken along line D-D of FIG. 8.

FIG. 8 is a side view of the sleeve 250. FIG. 9 is a cross-sectional view of the sleeve 250 taken along line C-C (which is orthogonal or substantially orthogonal to the longitudinal axis LA2 of the sleeve 250) of FIG. 8. FIG. 10 is another cross-sectional view of the sleeve 250. The sleeve 250 is movably coupled to the elongate member 210. In in the illustrated embodiment, the sleeve 250 defines a lumen 256. The lumen 256 extends from a first end portion 252 of the sleeve 250 to a second end portion 254 of the sleeve. The lumen 256 may receive at least a portion of the elongate member 210 such that the elongate member 210 may move or slide with respect to the sleeve 250.

The sleeve 250 is configured to retain the second end portion 214 of the elongate member 210 in its first or collapsed configuration. In the illustrated embodiment, the sleeve 250 includes a contact portion or a contact surface 259. The contact portion or the contact surface 259 is an inner surface of the sleeve 250 and is configured to contact the second end portion 214 of the elongate member 210 to help retain or force the second end portion 214 of the elongate member 210 in its first or collapsed configuration.

In the illustrated embodiment, the sleeve 250 includes an enlarged portion 257 disposed at the first or proximal end portion 252 of the sleeve 250. The enlarged portion 257 is configured to be larger than the remaining length of the sleeve 250. In some embodiments, the enlarged portion 257 is configured to help prevent the sleeve 250 from being entirely disposed within the body of the patient. For example, in some embodiments, the enlarged portion 257 is configured to contact another surface or outer portion of the body of the patient to help prevent the sleeve 250 from being entirely disposed within the body of the patient.

In the illustrated embodiment, the elongate member 210 has a length that is greater than a length of the sleeve 250. As best illustrated in FIG. 3A, the elongate member 210 has a length L1 along its longitudinal axis LA1 and the sleeve 250 has a length L2 along its longitudinal axis LA2. The length L1 is greater than the length L2.

In use, the medical device 200 may be inserted into a body of a patient (as schematically illustrated in FIG. 11). In some embodiments, the medical device 200 may be inserted into the body of the patient while the second end portion 214 of the elongate member 210 is in its first or collapsed configuration. For example, in some embodiments, the medical device 200 may be inserted into the body of the patient while the contact portion or contact surface 259 of the sleeve 250 is in contact with the second end portion 214 of the elongate member 210 to retain the second end portion 214 of the elongate member 210 in its first or collapsed configuration. In some embodiments, the medical device 200 may be inserted into the body of the patient while the second end portion 214 of the elongate member 210 is disposed within the lumen 256 of the sleeve 250.

In some embodiments, the medical device 200 may be inserted into the body of the patient such that the second or distal end portion 214 of the elongate member 210 is disposed within the body of the patient and the first or proximal end portion 212 of the elongate member 210 is disposed outside of the body of the patient (or extends from the body of the patient). As illustrated in FIG. 11, a distal end portion 202 of the medical device 200 extends from an outer surface OS of the body of the patient.

The second end portion 214 may then be moved from its first or collapsed configuration to its second or expanded configuration. For example, in some embodiments, the elongate member 210 is moved with respect to the sleeve 250 such that the contact portion or contact surface 259 of the sleeve 250 disengages or is removed from the second end portion 214 of the elongate member 210. For example, in the illustrated embodiment, the sleeve 250 may be moved in the direction of arrow M (as illustrated in FIG. 3A) to disengage the contact portion or the contact surface 259 from the second end portion 214 (i.e., remove the second end portion 214 from the lumen 256 of the sleeve 250).

The second end portion 214 of the elongate member 210 may then move to its second or expanded configuration. In some embodiments, the second end portion 214 of the elongate member 210 is biased to its second or expanded configuration and will move to such configuration in the absences of an external or retaining force.

In the illustrated embodiment, once the sleeve 250 is moved such that the second end portion 214 of the elongate member 210 extends from the sleeve 250 (as illustrated in FIG. 3A), the position of the elongate member 210 with respect to the sleeve 250 may be locked or fixed. In the illustrated embodiment, the elongate member 210 may be rotated in the direction of arrow N to lock or fix the elongate member 210 with respect to the sleeve 250. For example, in some embodiments, an inner surface 251 of the sleeve 250 may include a cam or otherwise uneven surface. As the elongate member 210 is rotated or twisted, the inner surface may frictionally couple the elongate member 210 to the sleeve 250. The elongate member 210 may be rotated in an opposite direction to disengage or unlock the elongate member 210 from the sleeve. In other embodiments, a different type of coupling mechanism may be used to removably couple or fix the elongate member 210 with respect to the sleeve 250. In some embodiments, the coupling mechanism used to removably couple or fix the elongate member 210 with respect to the sleeve 250 is a helical threaded screw type mechanism. For example, the elongate member 210 may be rotated with respect to the sleeve 250 to move the elongate member 210 linearly with respect to the sleeve 250.

In some embodiments, the second end portion 214 of the elongate member 210 is configured to retain or help retain the medical device 200 in place within the body of the patient. Specifically, as illustrated in FIG. 11, the second end portion 214 in its second or expanded configuration is configured to contact bodily tissue BT of the patient to retain or help retain the medical device 200 in place within the body of the patient.

In some embodiments, once the medical device 200 is disposed within the body of the patient, other medical devices may be inserted into the body of the patient though the lumen 216 defined by the elongate member 210. Accordingly, such other or secondary medical devices may be used to perform additional medical procedures once such device is disposed within the body of the patient.

In the illustrated embodiment, the proximal end portion 212 of the elongate member 210 includes a hub 230. The hub 230 defines a lumen 232. The lumen or opening 232 of the hub is in fluid communication with the lumen 216 of the elongate member 210. In the illustrated embodiment, the lumen or opening 232 of the hub 230 is tapered or funnel shaped. In other words, there is a portion of the opening or lumen that is larger or wider than another portion of the opening or lumen. In the illustrated embodiment, the lumen or opening of the hub 230 funnels down to the lumen 216 of the elongate member 210.

In some embodiments, the funnel shaped lumen 232 of the hub 230 may help funnel the secondary medical devices down to and guide them to the lumen 216 of the elongate member 210. For example, in the illustrated embodiment, an inner surface 234 of the hub 230 may guide secondary medical devices into the lumen 216 of the elongate member 210. Additionally, in some embodiments, the inner surface 234 may contact the secondary medical devices and help couple or retain the secondary medical devices in place once they are disposed within the lumen 216 of the elongate member 210. For example, in some embodiments, the inner surface 234 may frictionally retain or couple the secondary medical devices in place within the medical device 200. As best illustrated in FIG. 3B, in the illustrated embodiment, the hub 230 includes a lever 239. The lever 239 is configured to be moved to from a first position to a second position to contact the secondary medical device SMD to help couple the secondary medical device within the lumen 216 of the elongate member 210. In some embodiments, the lever 239 may be rotated or twisted to move into and out of engagement with the secondary medical device.

Figure 12:
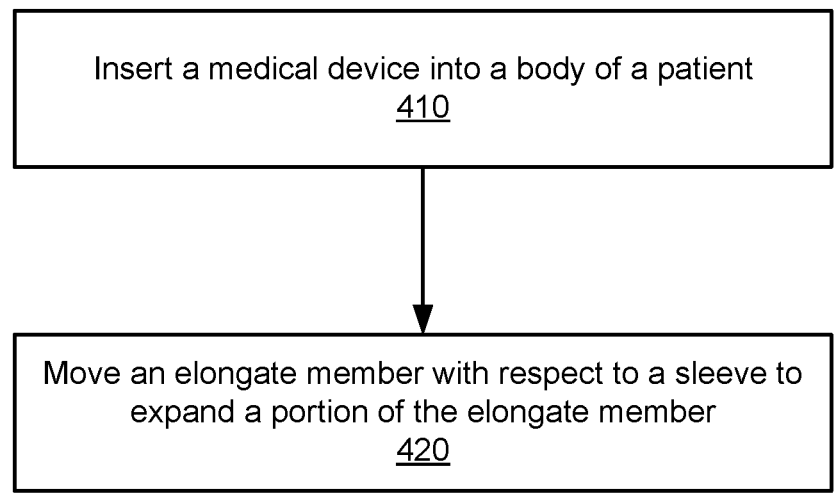
FIG. 12 is a flow chart of a method according to an embodiment.

FIG. 12 is a flow chart of a method 400 according to an embodiment of the invention. At 410, a medical device is inserted into a body of a patient. At 420, the elongate member of the medical device is moved with respect to the sleeve of the medical device. The movement allows a portion of the elongate member to move from a collapsed configuration to an expanded configuration. Accordingly, in some embodiments, the expanded configuration of the elongate member helps secure or anchor the medical device within the body of the patient.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. A medical device comprising:
an elongate member defining a lumen and having a first end portion and a second end portion, the first end portion having a hub member defining a funnel shaped opening, the second end portion having a first configuration and a second configuration, the second end portion having a first size when the second end portion is in the first configuration and a second size when the second end portion is in the second configuration, the first size being smaller than the second size, the second end portion being biased to the second configuration;
a sleeve defining a lumen extending from a first end portion of the sleeve to a second end portion of the sleeve, the lumen being configured to movably receive at least one portion of the elongate member, the sleeve being configured to engage the second end portion of the elongate member to help retain the second end portion of the elongate member in the first configuration; and
a lever extending through a sidewall of the hub member of the elongate member and into the funnel shaped opening defined by the hub member.

2. The medical device of claim 1, wherein the lumen defined by the elongate member extends from the first end portion of the elongate member to the second end portion of the elongate member.

3. The medical device of claim 1, wherein the elongate member defines a longitudinal axis, the at least one portion of the elongate member being movably received by the sleeve such that the elongate member may move in a direction substantially parallel to the longitudinal axis of the elongate member.

4. The medical device of claim 1, wherein the elongate member is configured to rotate with respect to the sleeve.

5. The medical device of claim 1, wherein the elongate member having a longitudinal length, the sleeve having a longitudinal length, the longitudinal length of the elongate member being greater than the longitudinal length of the sleeve.

6. The medical device of claim 1, wherein the second end portion of the elongate member includes a plurality of support members.

7. The medical device of claim 1, wherein the elongate member is configured to be locked in position with respect to the sleeve.

8. The medical device of claim 1, wherein the elongate member is configured to be locked in position with respect to the sleeve via a frictional coupling between a portion of the elongate member and a portion of the sleeve.

9. The medical device of claim 1, wherein the elongate member includes a first locking feature, the sleeve includes a second locking feature, the first locking feature being configured to engage the second locking feature to lock the elongate member with respect to the sleeve.

10. The medical device of claim 1, wherein the lumen of the elongate member is configured to receive a secondary medical device.

11. The medical device of claim 1, wherein the sleeve includes an inner surface, at least a portion of the inner surface of the sleeve being configured to engage the second end portion of the elongate member to help retain the elongate member in the first configuration.

12. A medical device comprising:
an elongate member defining a lumen and having a first end portion and a second end portion, the first end portion having a hub member defining a funnel shaped opening, the second end portion having a first configuration and a second configuration, the second end portion having a first size when the second end portion is in the first configuration and a second size when the second end portion is in the second configuration, the first size being smaller than the second size, the second end portion being biased to the second configuration;

a sleeve movably coupled to the elongate member, the sleeve having a contact surface, the contact surface being configured to contact the second end portion of the elongate member to help retain the elongate member in the first configuration, a first end portion of the sleeve having a first size, a second end portion of the sleeve having a second size, the second size of the sleeve being smaller than the first size of the sleeve; and a lever extending through a sidewall of the hub member of the elongate member and into the funnel shaped opening defined by the hub member.

13. The medical device of claim 12, wherein the elongate member is configured to rotate with respect to the sleeve.

14. The medical device of claim 12, wherein the second end portion of the elongate member includes a plurality of support members.

15. A method comprising:

inserting a medical device into a body of a patient, the medical device including an elongate member and a sleeve;

moving the elongate member with respect to the sleeve such that an end portion of the elongate member moves away from an end portion of the sleeve and moves from a collapsed configuration to an expanded configuration, a first end portion of the sleeve having a first size, a second end portion of the sleeve having a second size, the second size being smaller than the first size, the first end portion of the sleeve being configured to remain outside of the body of the patient; and coupling a secondary medical device within a lumen defined by the elongate member using a lever that extends through a sidewall of a hub member of the elongate member and into a funnel shaped opening of the hub member.

16. The method of claim 15, wherein the moving of the elongate member with respect to the sleeve includes rotating the elongate member with respect to the sleeve.

\* \* \* \* \*